United States Patent [19]

Stiefel

[11] 4,190,607
[45] Feb. 26, 1980

[54] METHOD FOR THE PREPARATION OF 2,3-DIMETHYL-PENT-4EN-ALDEHYDE

[75] Inventor: Frank J. Stiefel, Princeton Junction, N.J.

[73] Assignee: Carter-Wallace, Inc., New York, N.Y.

[21] Appl. No.: 947,201

[22] Filed: Sep. 29, 1978

[51] Int. Cl.$^2$ ............................................. C07C 47/20
[52] U.S. Cl. ................................................. 260/601 R
[58] Field of Search ...................... 260/601 R; 560/844

[56] References Cited

FOREIGN PATENT DOCUMENTS

| | | |
|---|---|---|
| 615484 | 4/1962 | Belgium . |
| 1377140 | 2/1965 | France . |
| 803059 | 10/1958 | United Kingdom . |
| 991978 | 5/1965 | United Kingdom . |
| 1015911 | 1/1966 | United Kingdom ............... 260/601 R |

OTHER PUBLICATIONS

Yale, J. Am. Chem. Soc. 72, 3710–3716, (1950).

*Primary Examiner*—Werren B. Lone
*Attorney, Agent, or Firm*—Kevin B. Clarke

[57] ABSTRACT

A process for the production of 2-methyl-2-sec. butyl-1,3-propanediol from crotyl alcohol is disclosed. The diol obtained is useful in the manufacture of 2-methyl-2-(1-methylpropyl)-1,3-propanediol dicarbamate a valuable antihypertensive agent.

6 Claims, No Drawings

METHOD FOR THE PREPARATION OF 2,3-DIMETHYL-PENT-4EN-ALDEHYDE

The present invention relates to certain novel methods for the preparation of 2-methyl-2-(sec butyl)-1,3-propanediol which compound may be converted to mebutamate (2-methyl-2-secbutyl-1,3-propanediol dicarbamate) by reaction with phosgene and subsequent ammoniation. Mebutamate is useful as CNS depressant or an antihypertensive. More particularly, this invention relates to a novel method which includes the process steps of reacting crotyl alcohol with allyl chloride to obtain allyl crotyl ether and subsequent rearrangement of the ether to 2,3-dimethyl-pent-4en-aldehyde. The aldehyde is converted to the propanediol and subsequently to mebutamate by known methods.

Mebutamate has been known for more than twenty years first being described in U.S. Pat. No. 2,878,280.

Mebutamate is prepared from 2-methyl-2-(sec butyl), 3-propanediol (mebutamate diol). There are many potential methods available for the preparation of the required 2,2-disubstituted 1,3-propanediol such as disclosed in U.S. Pat. Nos. 3,359,324 and 2,937,119 as well as British Pat. Nos. 803,059; 991,978 and 1,015,911; Belgium Pat. No. 615,484; French Pat. No. 1,377,140 and numerous other publications such as H. Yale (J. Am. Chem. Soc., 72, 3710-6, 1950).

The processes currently available suffer from deficiencies such as low overall yield, high product cost or the nonavailability of the necessary intermediate. Accordingly, a new route to 2-methyl-2-(sec butyl)-1,3-propanediol is highly desirable.

I have now found a novel method for producing mebutamate diol which includes the process steps of reacting crotyl alcohol and allyl chloride to produce a mixture of isomers of allyl crotyl ether, heating said crotyl ether to produce 2,3-dimethyl-pent-4en-aldehye. The aldehyde is then converted to 2-methyl-2-(sec butyl)-1, 3-propanediol by reacting 2,3-dimethyl-pent-4en-aldehyde and formaldehyde to produce 2,3-dimethyl-2-hydroxymethyl-pent-4en-ol and subsequently hydrogenating the said alcohol in the presence of a catalyst to produce 2-methyl-2-(sec butyl)-1,3-propanediol.

Alternatively, if desired, 2,3-dimethyl-pent-4en-aldehyde is partially hydrogenated to produce 2,3-dimethylpentaldehyde and subsequently reacting said aldehyde with formaldehyde in the presence of a basic catalyst to produce 2-methyl-2-(sec butyl)-1,3-propanediol.

This procedure may be further varied in that the 2,3-dimethyl-pent-4en-aldehyde can be fully hydrogenated under hydrogenating conditions to saturate the olefinic bond as well as reduce the aldehyde group to an alcohol group and produce 2,3-dimethylpentanol with subsequent dehydrogenation of said pentanol to produce 2,3-dimethylpentaldehyde which is then reacted with formaldehyde to produce mebutamate diol.

The reactions whereby mebutamate diol is produced in accordance with the methods of the invention can be illustrated by the following series of reaction schemes whereby crotyl alcohol allyl chloride are combined in homogeneous mixture and condensed to produce allyl crotyl ether:

CH₃CH=CHCH₂OH + CH₂=CHCH₂CL ⟶

I          II

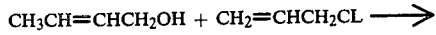

-continued

CH₃CH=CHCH₂OCH₂CH=CH₂

III

The above reaction is carried out in the presence of a condensation agent such as sodium metals, NaH, NaOH, KOH, K₂CO₃ and the like in amounts ranging from about a mole to mole equivalent in the case of NaH and sodium metals to large excess of K₂CO₃. The proportion of crotyl alcohol to allyl chloride can be varied over the range of from about 1.0 moles to about 1.3 moles allyl chloride per mole of crotyl alcohol.

The reaction is carried out at a temperature range of from about 50° C. to about 80° C. The temperature range is not critical and is dependent only upon the rate of reaction time desired.

The solvent employed is dimethyl formamide, dimethylacetamide, toluene, benzene or other suitable material which is a solvent for the reactants and which will not interfere with the reaction.

The allyl crotyl ether is then converted to 2,3-dimethyl-pent-4en-aldehyde by a transition metal catalyzed rearrangement as illustrated below:

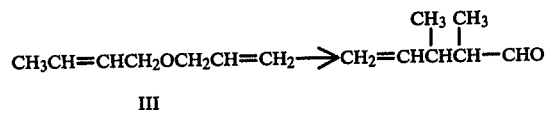

III

Surprisingly, the rearrangement reaction can be carried out at relatively low vapor temperatures of 125°-136° C. and ambient pressure. Suitable catalysts for use in the reaction are the transition metals such as rubidium, molybdenum, ruthenium and palladium, preferably ruthenium (II) such as described by Reuter and Salomon (J. Org. Chem., Vol. 42, No. 21, 1977, pp. 3360-3364).

The 2,3-dimethyl-pent-4en-aldehyde is then converted to the mebutamate diol in the manner described in U.S. Pat. No. 3,359,324 which description is hereby incorporated by reference.

The following examples serve to illustrate the invention only and are not intended in anyway to limit or otherwise effect the scope of the invention which is set forth in the appended claims.

EXAMPLE 1

ALLYL CROTYL ETHER 72 g. of 50% sodium hydride dispersed in oil is added to a one liter three neck, round bottom flask containing 100 ml. of dimethyl formamide. A homogeneous mixture of 108 g. crotyl alcohol and 143 g. allyl chloride is added dropwise with stirring. The reaction temperature is maintained between 50° and 60° C. and the addition is completed in one hour. The reaction is stirred for one hour followed by decomposition with 300 ml. of water. The pH of the mixture is adjusted to between 4 and 5 with glacial acetic acid and the aqueous and organic layers are separated. The aqueous layer is extracted with 75 ml. of pentane and the extract combined with the organic phase. The organic phase is washed twice with 100 ml. of water and then dried over sodium sulfate. The mixture is filtered and distilled yielding 122 g. of allyl crotyl ether B.P. 125°-127° C.

EXAMPLE 2

2,3-DIMETHYL-PENT-4EN-ALDEHYDE 122 g. of allyl crotyl ether is placed in a 300 ml. three neck round bottom flask. 10 mg. of tris (triphenyl phosphine) ruthenium dichloride is added and the mixture is brought to reflux at a vapor temperature of 125° C. to 136° C. and refluxed overnight. The product 2,3-dimethyl-pent-4en-aldehyde which has a boiling point of 133°–134° C. can be used as is or distilled.

EXAMPLE 3

2-METHYL-2(Sec Butyl)-1,3-PROPANEDIOL 50 g. of 2,3-dimethyl-pent-4en-aldehyde is added to 100 ml. of 37% formaldehyde in a 250 ml. round bottom flask. 70 g. of a 50% w/w solution of sodium hydroxide is dripped into the mixture with stirring and the temperature maintained at 35°–40° C. with an ice bath. When the addition is complete the mixture is stirred one-half hour at room temperature and the two layers separated. The aqueous layer is extracted with 75 ml. ethyl acetate and the extract combined with the organic layer. The organic layer is washed twice with 100 ml. of water. The organic layer is placed in a Parr hydrogenation bottle and diluted to 150 ml. with methanol. 1 g. wet Raney Nickle catalyst is added and the mixture reduced at 50 p.s.i. until no more hydrogen is absorbed. The catalyst is removed by filtration and the filtrate concentrated and distilled. A yield of 45.4 g. of 2-methyl-2(sec butyl)-1,3-propanediol BP 139°–140° C. at 10 mm. pressure and refractive index $N_D^{22}=1.4610$ is obtained.

The useful antihypertensive agent mebutamate is produced by well know methods such as by bubbling phosgene gas through a liquid mixture of mebutamate diol until at least one mole of phosgene per hydroxyl equivalent has been consumed and the 2-methyl-2-(sec butyl)-1,3-propanedichloroformate is produced. The same is reacted with ammonia to produce mebutamate.

Alternatively, ammonia and phosgene gas can be reacted with the diol in anhydrous solvent to produce mebutamate.

I claim:

1. A method for preparing 2,3-dimethyl-pent-4en-aldehyde which comprises heating allyl crotyl ether at a temperature of 125°–136° C. and ambient pressure in the presence of a transition metal catalyst selected from the group consisting of molybdenum, palladium, rubidium and ruthenium.

2. A method according to claim 1 wherein said catalyst is tris (triphenyl phosphine) ruthenium dichloride.

3. A method for preparing 2,3-dimethyl-pent-4en-aldehyde which comprises adding a mixture of crotyl alcohol and allyl chloride to a condensing agent in a Solvent selected from the group comprising dimethyl formamide, dimethyl acetamide, toluene and/or benzene to produce allyl crotyl ether, heating said allyl crotyl ether at a temperature of 125°–136° C. and ambient pressure with a transition metal catalyst and selected from the group consisting of molybdenum, palladium, rubidium and ruthenium and recovering the 2,3-dimethyl pent-4en-aldehyde produced thereby.

4. A method according to claim 3 wherein said condensing agent is sodium hydride.

5. A method according to claim 3 wherein said solvent is dimethyl formamide.

6. A method according to claim 3 wherein said catalyst is tris (triphenyl phosphine) ruthenium dichloride.

* * * * *